United States Patent
Thuruthiyil et al.

(10) Patent No.: US 6,849,469 B1
(45) Date of Patent: Feb. 1, 2005

(54) MONITOR AND CONTROL OF SILICIDATION USING FOURIER TRANSFORM INFRARED SCATTEROMETRY

(75) Inventors: Ciby Thomas Thuruthiyil, Fremont, CA (US); Bhanwar Singh, Morgan Hill, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/677,043

(22) Filed: Oct. 1, 2003

(51) Int. Cl.⁷ ............................................... H01L 21/00
(52) U.S. Cl. ............................ 438/7; 438/5; 438/682; 118/663; 118/688
(58) Field of Search ....................... 438/7, 5, 14, 682; 118/663, 688, 691

(56) References Cited

U.S. PATENT DOCUMENTS

| | | | |
|---|---|---|---|
| 5,769,540 A | * | 6/1998 | Schietinger et al. ........ 374/127 |
| 5,883,518 A | | 3/1999 | Borden |
| 6,166,354 A | * | 12/2000 | Hause et al. ................ 219/390 |
| 6,429,141 B1 | | 8/2002 | Van Ngo et al. |
| 6,559,457 B1 | | 5/2003 | Phan et al. |

OTHER PUBLICATIONS

R.J. Schreutelkamp, et al. "In situ emissivity measurements to probe the phase transformations during rapid thermal processin Co. silicidation" Appl. Phys. Lett. vol. 61, INo. 19, pp. 2296–2298 (Nov. 9, 1992).*

Youngjae Kwon, Chongmu Lee, Silicidation behaviors of Co/Ti/ and Co/Hf bilayers on doped polycrystalline Si substrate, Materials Science & Engineering, Jul. 19, 1999.

* cited by examiner

*Primary Examiner*—Caridad Everhart
(74) *Attorney, Agent, or Firm*—Amin & Turocy, LLP (57) ABSTRACT

Real-time analysis and control of a semiconductor silicidation process. The architecture includes system and methods for monitor and control of a silicidation process during rapid thermal anneal. An FTIR system analyzes selected and/or random regions where silicidation is occurring, and signals the process control system to control the process according to the status of the analyzed silicide formations.

44 Claims, 7 Drawing Sheets

MONITOR AND CONTROL OF SILICIDATION USING FOURIER TRANSFORM INFRARED SCATTEROMETRY

TECHNICAL FIELD

This invention is related to control systems for semiconductor fabrication, and more specifically, to a system that uses a UV/FTIR signal to monitor and control silicidation.

BACKGROUND OF THE INVENTION

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device densities, smaller and smaller feature sizes are required that include, for example, the width, depth, and spacing of interconnecting lines, spacing and size of memory cells, and surface geometry of various: features such as corners and edges. Such small feature characteristics require high-resolution photolithographic processes for pattern transfer between various media. A wafer is coated uniformly with a radiation-sensitive photoresist film, and an exposing source (such as optical light, x-rays, or an electron beam) illuminates selected areas of the wafer surface through an intervening master template mask for a particular pattern.

Layers of photoresist, conductive, polymeric and insulative materials are routinely applied to wafers multiple times during a manufacturing process for integrated circuits, as one of a sequence of steps to produce a desired lithographic pattern. Thickness and uniformity of the layers is critical to the overall functionality of the manufactured device. The goal of the photoresist application process as well as subsequent layering processes is to achieve uniform layers on the wafer surface. This goal can be achieved by planarizing the layers in order to obtain a desired thickness and uniformity.

Metal silicides have excellent material properties. For example, a cobalt alloy ($CoSi_2$) has a very low resistivity, ability of uniform formation on very narrow polycrystalline-silicon ("poly-Si") lines, no reaction with dopants, and good resistance to dry etching. When cobalt silicide is applied in self-aligned processes, device operating speeds can be increased. However as devices are scaled down to deep submicron dimensions, the formation of stable and very shallow junctions which is essential to successful device fabrication becomes more difficult.

Silicide formation occurs in conjunction with an annealing process where the wafer is heated for a short period of time to form a metal silicide. Some silicidation processes may be performed in multiple annealing steps, for example, when using titanium ($TiSi_2$).

What is needed are improved silicidation processes in semiconductor fabrication.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention disclosed and claimed herein, in one aspect thereof comprises a technique that controls silicidation processes on a semiconductor substrate (e.g., a polycrystalline ("poly") layer) using a real-time feedback process of a UV (Ultraviolet)/FTIR scatterometry signal. In silicidation, silicides that include cobalt (Co), for example, may be deposited over a poly layer (patterning). Near-noble metal and refractory metal silicides have been applied to ULSI (Ultra Large Scale Integration) device fabrications in order to reduce the resistance of poly-silicon and to minimize the series resistance of source/drain regions. The near-noble metal silicide forms in contact with the silicon substrate while a silicide layer rich in the refractory metal forms at the top. A grating structure is then used at the poly layer. The UV/FTIR scatterometry signal is then used to monitor the silicide formation during a rapid thermal annealing (RTA) process. When the correct depth and silicide formation is achieved, the system analyzes the UV/FTIR signal to end the RTA process. This noncontact technique provides consistent control over formation and depth of the silicide formation for optimum device performance.

To the accomplishment of the foregoing and related ends., certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention may become apparent from the following detailed description of the invention when considered in conjunction with the drawings.

DETAILED DESCRIPTION OF THE INVENTION

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

Figure 1:
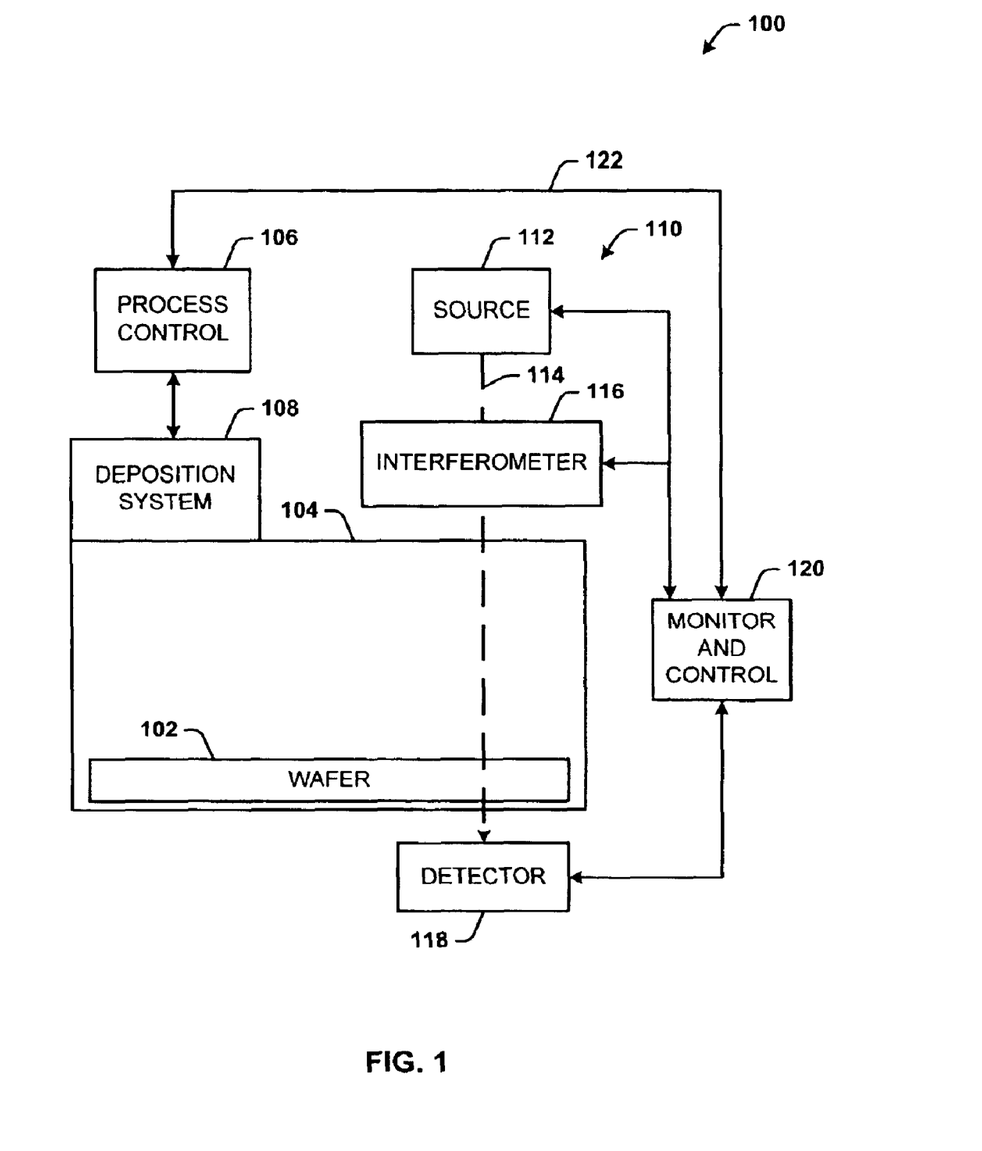
FIG. 1 illustrates a block diagram of a silicidation system that uses UV/FTIR analysis feedback in accordance with the present invention.

Referring now to FIG. 1, there is illustrated a block diagram of a silicidation system 100 that uses UV/FTIR analysis feedback in accordance with the present invention. Note that in the context of this application the processes associated with doping and the measurement thereof are considered to be different than those associated with a silicidation process. Conventional fabrication systems include the real-time measurement and analysis of doping profiles of a semiconductor substrate to control the fabrication process. There is provided a wafer 102 on which silicidation is performed. The wafer 102 is positioned and controlled in a process chamber 104 according to conventional processes. A process control subsystem 106 monitors and controls a process chamber subsystem 108 that facilitates the introduction and removal of gases, temperature and pressure control, and any other processes associated with semiconductor fabrication.

The general name "silicide" refers to the combination of metals (refractory or noble) with silicon that forms a Metal$_x$Si$_y$ compound under heat treatment. Silicidation is the formation process of a metal-silicon alloy by annealing or heat treatment. The main benefit of silicidation is the reduced resistivity provided by certain metal/silicon compounds. Silicides have been used for many years in the microelectronic industry to circumvent the high resistivity seen when contacting metal to polysilicon gates and source/drain regions of conventional MOSFET (Metal-Oxide Semiconductor Field Effect Transistor) structures. The silicide process involves incorporation of metal into silicon that is being contacted to reduce the resistivity of the contact. Different metals are chosen to create suicides based on their properties such as processing temperature, dry etch capabilities, wet etch chemicals necessary, resistivity, dominant diffuser species, etc.

Some of the specific applications of suicides include providing lower resistance on polysilicon gates, leading to a decrease in electrical response delay (critical for long gate lines). Silicides also enable bridging of dual-gate CMOS (Complementary Metal-Oxide Semiconductor) devices, and reduce contact resistance at CMOS source and drain structures. Silicides may be metallic, superconducting, or semiconducting, which makes them suitable for a variety of applications as active components, interconnects or nanoelectrodes for solid state or molecular electronic systems. Examples of metals that can be alloyed with silicon include one or more transition metals such as titanium, cobalt, molybdenum, iron, platinum, niobium, hafnium, vanadium, zirconium, chromium, calcium, nickel, tantalum, and tungsten.

Silicide advancements led to the development of "salicide" processes—self-aligned silicides, a crucial component in submicron CMOS technology. Salicides are possible due to the metal's selective reactivity, i.e., metals will react only with silicon, and will leave other materials on the wafer ($SiO_2$, $Si_3N_4$, etc.) intact.

Titanium silicide ($TiSi_2$), for example, is formed by depositing Ti over the polysilicon, followed by a two-step anneal. The first anneal is at low temperature, approximately 600° C. for about 15–60 seconds. Any unreacted Ti is then selectively etched off. After the first anneal, $TiSi_2$ is in a metastable "C49" temperature phase (approximately 600° C.). An 800° C. second anneal for approximately 30–60 seconds is required to transform $TiSi_2$ to the equilibrium "C54" phase, which has a lower resistivity in the range of 13–20 $\mu$Ohm-cm.

A process flow for combinations of metals (e.g., cobalt and nickel) and silicon types (polysilicon and crystalline silicon) may be the following. The substrate is first cleaned to remove particulates and contamination from the surface, followed by a buffered oxide etch to remove native oxide from the silicon wafer surface. Metal deposition is performed using sputtering along with a capping layer. When using cobalt, a two-step anneal process is preferred for cobalt silicide formation. The first step is at approximately 450° C. in inert ambient. Nickel silicide is typically formed in a single step at temperatures in the range of 400–500° C. The wafer is then etched to remove unreacted metal. The second anneal step for cobalt silicide occurs at approximately 700° C. for approximately 25–50 seconds for the transition from CoSi to $CoSi_2$.

One method of analyzing materials during the fabrication process is by way of Fourier transform infrared (FTIR) spectroscopy. The infrared (IR) spectrum of an organic compound and some inorganic compounds serve as a unique fingerprint and provides specific information about chemical bonding and atomic structure. Since chemical bonds absorb IR energy at specific frequencies (or wavelengths), the general structure of compounds may be determined by the spectral locations of their IR absorptions. Plotting the compounds IR transmission versus its frequency, information unique to each compound can be found by comparing the data to reference spectra. This technique allows rapid analysis of micro-samples precise to the nanogram level in certain cases, making FTIR an invaluable tool.

FTIR is a technique that uses an interferometer for data collection and a digital Fourier transformation to process the data. In the context of semiconductor fabrication, IR radiation is passed through a water sample. Some of the infrared radiation is absorbed by the sample material and some of it is passed through (or transmitted). The resulting spectrum represents the molecular absorption and transmission, creating a molecular fingerprint of the wafer sample. Like a fingerprint, no two unique molecular structures produce the same infrared spectrum. This makes infrared spectroscopy useful for several types of analysis. However, such analysis tools are routinely used for manual inspection of fabrication processes. An FTIR analysis subsystem 110 is an integral component of the system 100 to facilitate real-time analysis of the silicidation process on the wafer 102, and includes a source 112 for emitting light 114, an interferometer 116, and a detector subsystem 118. The source 112 is a heated emitter source for emitting the light 114 across a spectrum of interest. The source 112 may be, for example, a conducting ceramic or wire heater coated with ceramic. The wafer 102 under process absorbs light according to its chemical properties at the point of inspection. The detector subsystem 118 collects the radiation that passes through the wafer 102, and outputs an electrical signal representative of the energy as a function of frequency or wavelength.

FTIR analysis operates to send all of the source light through the interferometer 116 and onto the wafer 102. The interferometer 116 includes a beamsplitter that sends the source light 114 in two directions at right angles. One beam intersects a fixed mirror and is reflected back to the beamsplitter. The other beam intersects a moving mirror, such that the motion of the mirror makes the total path length variable in contrast to the beam path taken by the fixed mirror. The moving mirror beam is also reflected back to the beamsplitter such that the two beams are recombined at the beamsplitter, but the path difference creates constructive and destructive interference, i.e., an interferogram. The interferogram is then Fourier transformed to a spectrum data format for processing.

The wafer 102 absorbs all of the different wavelengths according to its chemical characteristics at the point of inspection, which subtracts specific wavelengths from the interferogram. The detector subsystem 118 reports the variation in energy versus time for all wavelengths simultaneously to an FTIR monitor and control subsystem 120. The Fourier transform (FT) aspect allows for conversion of an intensity-versus-time spectrum into an intensity-versus-frequency spectrum. The monitor and control subsystem 120 digitizes the detector signal (if not already provided as a digitized signal from the detector system), and performs the transformation. A laser beam is also superimposed to provide a reference for FTIR operation. The monitor and control subsystem 120 also connects to both the source 112 and interferometer 116 for monitor and control thereof.

Once converted, the monitor and control subsystem 120 processes the FT information for comparison with predetermined FT information to determine if the silicidation process is complete or nearing completion. If so, the feedback aspect of the present invention involves sending a signal over a communication link 122 from the monitor and control system 120 to the process control subsystem 106 to initiate orderly termination of the silicidation process such that silicide formation is optimized. The feedback link may be a wired or wireless communication link that facilitates transmission of signals therebetween.

The detector subsystem 118 includes a detecting element (not shown) that senses the wavelength variations of the light 114 as it passes through the wafer 102. The output signals of the detecting element are fed to a preamplifier where the signals are converted in a voltage signal varying with time. The voltage signal is digitized with an A/D converter (not shown) of a certain bit resolution, e.g., 8, 16, 20, 32, or more. Higher bit resolutions are used to obtain better signal-to-noise ratios. The detector subsystem 118 is triggered for sampling by a trigger circuit and fringe detector (not shown), which may be included as part of the detector subsystem 118.

It is to be appreciated that the capabilities of the monitor and control subsystem 120 of the FTIR subsystem 110 may be included as part of the process control subsystem 106 or vice versa, such that there is only a single monitor and control subsystem for process control and FTIR analysis in the system 100 (denoted generally as a control system), wherein this single control system receives the output of the detector subsystem 118, and also controls the fabrication processes. It is further to be appreciated that the link 122 may form part of a network such that monitor and control data of the monitor and control system 120 may be accessed and processed remotely, for example, by a remote system disposed on the network.

The advantages of the disclosed architecture may be obtained whether performing FTIR mapping or imaging, and with the use of other microspectroscopic instrumentation, for example, a microscope, for the detection of chemical species from a specific spatial region.

To provide a more representative sampling of the formation process the wafer 102 and/or the FTIR subsystem 110 may be controlled such that random samples of silicidation regions of the wafer may be analyzed during the formation process to obtain an average result. This is facilitated through the use of a grating pattern. A grating structure may he used to facilitate monitoring formation of the silicide during the silicidation process at any number of distinct regions of the wafer. For example, if a wafer has a grating pattern (not shown) imposed thereon that subdivides the wafer into one-hundred forty-four regions (denoted $X_1Y_1 \ldots X_{12}Y_{12}$), the FTIR subsystem 110 may be controlled to analyze the silicidation process during formation at each of the regions or at selected regions. In response, where a given region is exhibiting an undergrowth of silicide, the process system may be controlled to increase the formation process, generally, at that region to "catch that region up" with the overall process. Similarly, if the subsystem 110 (either directly or indirectly through the process subsystem) senses that the formation process is proceeding too quickly in given region(s), the formation process may be slowed by controlling the heat process accordingly.

An exemplary system for in-situ detection and reduction of closed area defects on a wafer may employ the FTIR technology that operates in accordance with the description provided herein. Another exemplary system for in-situ detection may employ one or more light sources arranged to project light onto the grating pattern developed on a wafer and one or more light detecting devices (e.g., photo detector, photodiode) for detecting light signatures reflected by the grating. The light signature reflected from the grating (and wafer) is characteristic of the presence (or absence) of closed area defects (e.g., intrusion defects, extrusion defects, corner defects, pinhole defects).

The wafer 102 may be scanned, moved, or rotated for analysis of any number of regions such that sample regions may be analyzed by the FTIR subsystem 110 in order to provide a more reliable measure of not only the state of the silicide formation process, but any processes performed during fabrication. This capability further facilitates data acquisition and analysis for developing historical, as well as trend data during fabrication processes. Such data may be used to track equipment wear, process calibration, wafer surface imperfections in selected regions, and many other data points. For example, if during inspection it is found that a certain region of the wafer is exhibiting surface irregularities during a given process, this information may be used to affect the fabrication process by feeding back this inspection information for processing by the monitor and control subsystem 120 to signal the process control subsystem 106 to, for example, extend the process in an attempt to correct the problem, or take some other action to correct or reduce the effects of the surface irregularities. Not only can the inspection data be used across regions of a single wafer, but also from the inspection of many wafers in a single process or multiple processes. For example, if it determined that a certain region of multiple wafers is exhibiting flaws, this information may also be used to control the process subsystem 106 in manner that can correct such flaws in a current batch or later batch. Thus the capability of the present invention to inspect and control the fabrication processes in real-time offers a significant advantage in ultimately providing a successful semiconductor product.

Figure 2:
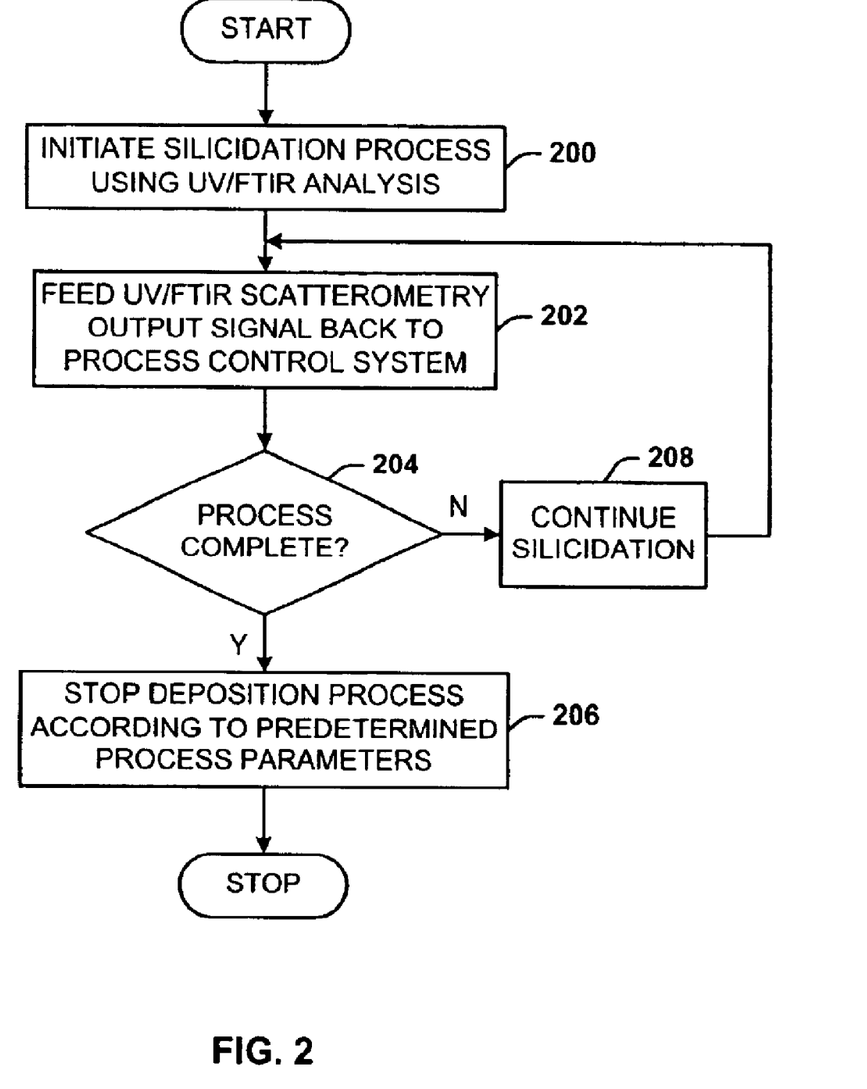
FIG. 2 illustrates a flow chart of the process for achieving optimum deposition and feature characteristics in accordance with the present invention.

Referring now to FIG. 2, there is illustrated a flow chart of the process for achieving optimum deposition and feature characteristics in accordance with the present invention. While, for purposes of simplicity of explanation, the one or more methodologies shown herein, e.g., in the form of a flow chart, are shown and described as a series of acts, it is to be understood and appreciated that the present invention is not limited by the order of acts, as some acts may, in accordance with the present invention, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

At 200, the silicidation process is started using UV/FTIR analysis of fabrication features. At 202, an output signal of the FTIR analysis subsystem is fed back to the process control system. As indicated above, this signal may be transmitted either directly thereto or indirectly through the FTIR monitor and control subsystem. At 204, it is determined, based upon the output signal, whether the silicidation process is complete or nearing completion. Thus, the output signal is processed against predetermined process criteria to determine if the criteria have been met. If YES, flow is to 206 to stop the deposition process. Flow then reaches a Stop block. If NO, flow is from 204 to 208 to continue the silicide formation process. Flow then loops back to the input of 202 to continue processing the scatterometry output signal.

Figure 3:
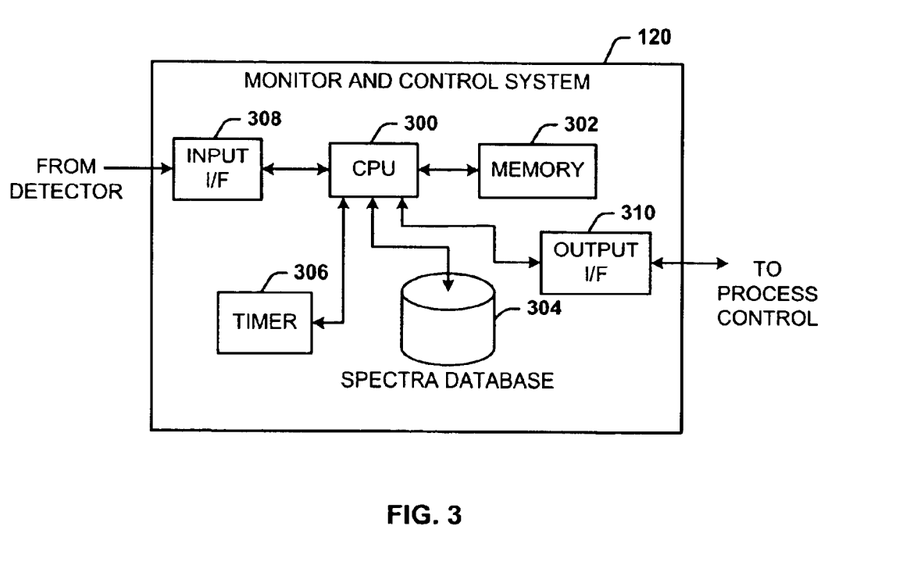
FIG. 3 illustrates a block diagram of the monitor and control system.

Referring now to FIG. 3, there is illustrated a block diagram of the monitor and control system 120. The system 120 includes a processor (CPU) 300 for controlling all system functions. The system 120 also includes a memory 302 connected to the CPU 300 for storing routines, programs, and data during operation of the system 120. A database 304 is provided in communication with the CPU 300 for mass storage of spectra data, programs, and other software information for operating the system 120 in accordance with the present invention. The stored data include rapid thermal annealing (RTA) profile information for various silicides used in silicidation processes. The profile information defines the state of the silicidation for various suicides over time as analyzed by an FTIR system. Thus if silicidation for a particular $CoSi_2$ formation process normally takes twenty seconds, profile information may include the FTIR spectra data related at times, for example, five, ten, fifteen, and twenty seconds. The system 120 will then take FTIR "snapshots" at the corresponding times for comparison with this profile data to monitor annealing over the duration of the process. In support thereof, the system 120 also includes a timing capability provided by a timer 306 in communication with the CPU 300, which timing capability may be via hardware and/or software.

The system 120 also includes an input interface (I/F) 308 and an output I/F 310 for facilitating the communication of signals and data. For example, the input I/F 308 communicates at least with the detector subsystem to facilitate detecting, capturing, and digitizing FTIR spectra from the inspection point structures of the wafer. As indicated hereinabove, the detector subsystem may provide the digitized spectra data. Alternatively, the detector subsystem may provide raw analog data to the system 120 for digitization and processing. The output I/F 310 facilitates communicating output signals and data to at least the process control subsystem to control the annealing process. The output I/F 310 may include wired and/or wireless transceiver capabilities for wireless communication of signals and/or data to the process control subsystem or other systems suitably configured. In any case, the system 120 provides an input to the process control subsystem such that the RTA process may be controlled in response to the status and quality of the FTIR spectra data.

The monitor and control system 120 may also include a microscope (not shown) for inspection site or region viewing, which view may be captured via video or images for presentation to a user via a monitor or display (not shown).

Figure 4:
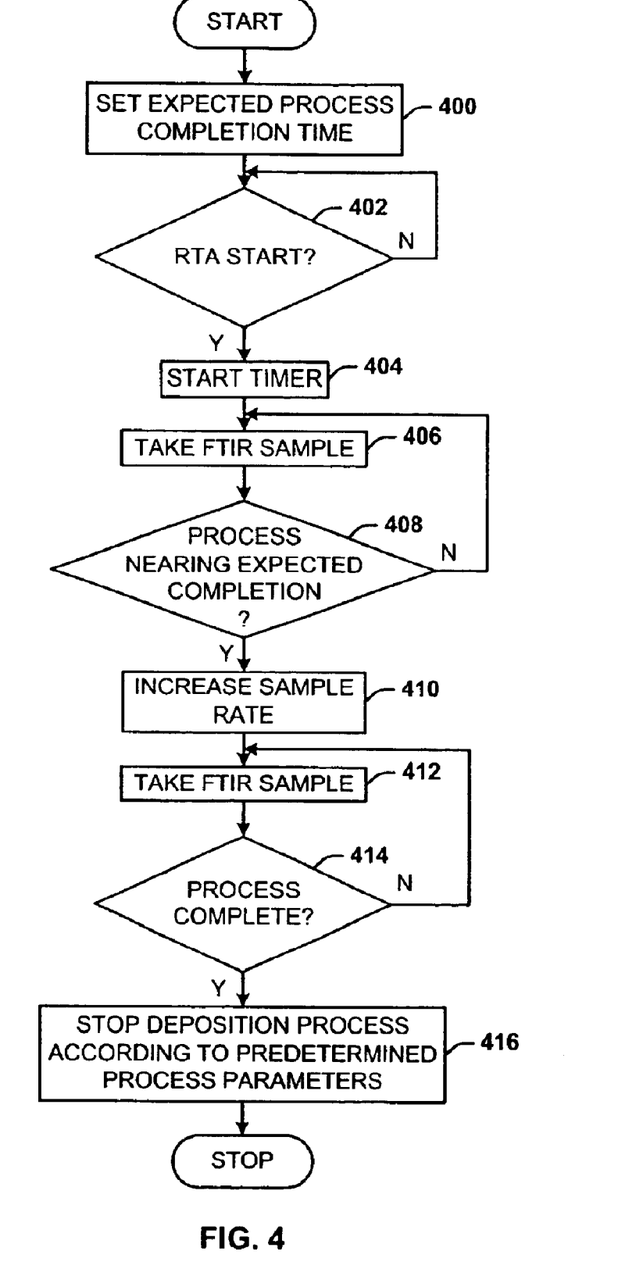
FIG. 4 illustrated a flow chart of an exemplary FTIR data acquisition and control process in accordance with the present invention.

Referring now to FIG. 4, there is illustrated a flow chart of an exemplary FTIR data acquisition and control process in accordance with the present invention. A goal of the disclosed feedback architecture is to provide an optimized real-time annealing process during silicidation of semiconductor layers. In this particular example, as the expected end of the process is approached, sampling is increased to more accurately control the RTA process. At 400, the monitor and control system 120 sets the expected time for the particular silicide and annealing process to be monitored. At 402, the monitor and control system checks for the start of the RTA process, as provided by the process control system. If NO start signal is receive, flow loops back to the input of 402 to continue checking for the start signal. If the start signal is received, for is from 402 to 404 to start the system timer according to the expected time for the particular RTA process. At 406, the system signals the FTIR subsystem to take a sample, which sample is then processed to determine the state and quality of the RTA process at that point of interest on the wafer. At 408, a check is made to determine of the RTA process is nearing completion. If NO, flow loops back to the input of 406 to facilitate taking another sample at the designated time. That is, if the sample rate is 1 Hz, the next sample is taken one second from the previous sample time.

If the system determines in accordance with predetermined process completion time that the RTA process is nearing completion, flow is from 408 to 410 to increase the sampling rate. That is, if the previous sampling rate was 1 Hz, the sampling may be doubled to 2 Hz or greater to more closely monitor the process as it nears completion. At 412, another sample is taken at the new sample rate and processed. At 414, the system determines if the RTA process is complete. This determination can be made in accordance with one or more different criteria. Preferably, the FTIR analysis provides sufficient resolution such that the actual process spectra data may be used as a trigger for ending the RTA process. That is, although the RTA process has an expected completion time of, for example, twenty seconds, real-time data analysis may indicate that optimum structure formation occurs at 19.75 seconds, or 20.25 seconds, such that the monitor and control system signals the process control system to control the silicidation process accordingly to achieve optimum formation.

It is to be appreciated that data interpolation may be used to more closely control the process. That is, if sampling is 2 Hz, the system may compute the estimated spectra data for process times between the sample times such that the silicidation process may be more precisely controlled. Based upon the interpolation data, the system may be controlled automatically to dynamically change the sampling rate instead of using a predetermined stepped sampling rate when the expected process completion time approaches. For example, if the interpolation data indicates a slope such that the process is rapidly approaching completion much faster than anticipated, the system may automatically ramp up the sampling rate according to some stepped criteria to more closely control the process, and when the data slope is less, reduce the sampling rate until the process end approaches.

Figure 5:
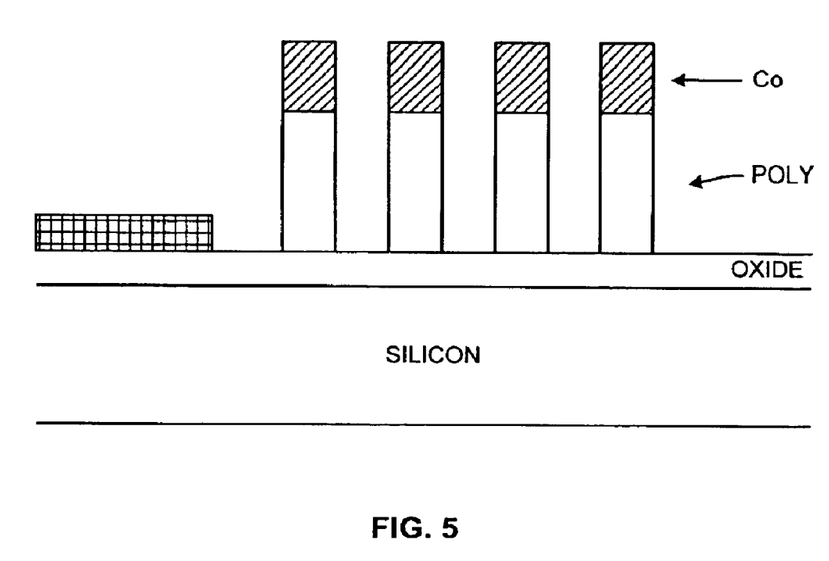
FIG. 5 illustrates a sectional view of a silicidation process using cobalt on poly.

Referring now to FIG. 5, there is illustrated a sectional view of a silicidation process using cobalt on poly. Here the patterned poly layer has four fabricated structures on which cobalt is formed. A grating structure is used at the poly layer. The UV/FTIR analysis subsystem is used to monitor the silicide formation during the RTA process. When the correct depth and silicide formation is achieved, the UV/FTIR output signal is fed back to the process controller to end the RTA process. This provides constant and consistent formation and depth of the cobalt formation for optimum device performance. Of course, the disclosed feedback architecture is not limited to cobalt and alloys thereof, but is also is operable to optimize silicidation using any silicide metals, including, but not limited to, titanium, tantalum, nickel, tungsten, and alloys thereof.

Figure 6:
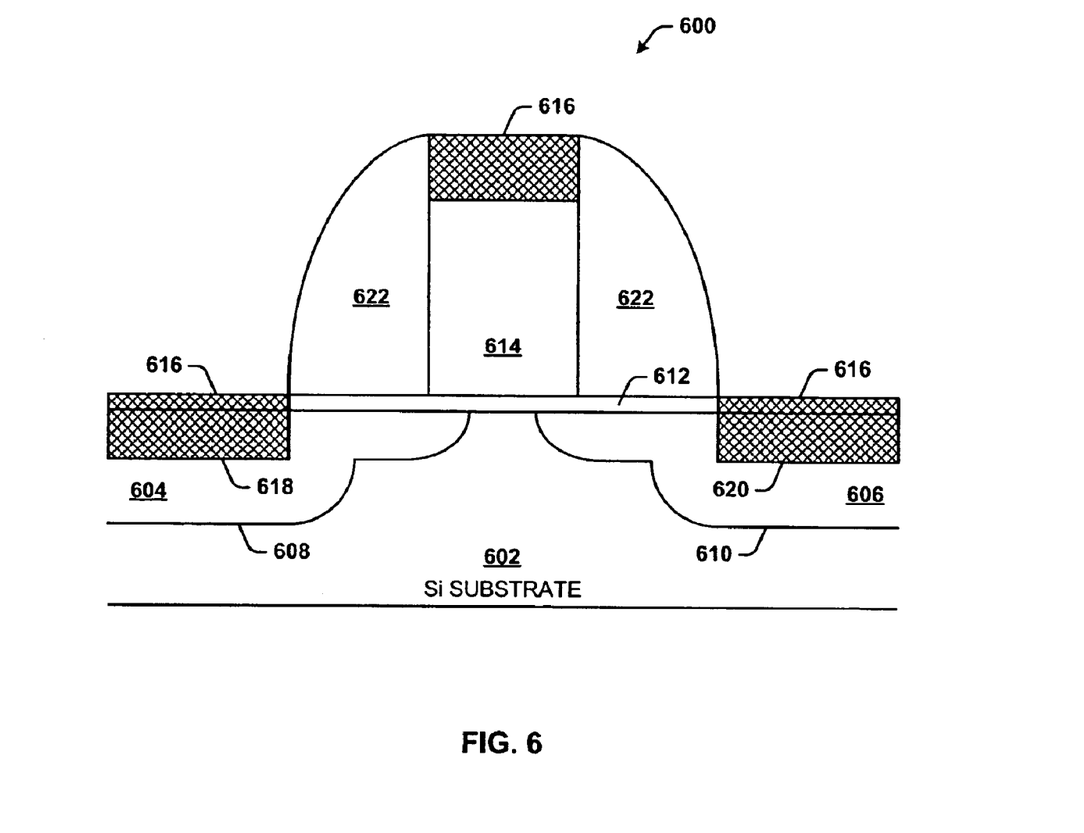
FIG. 6 illustrates a sectional view of a bulk MOSFET device the silicidation process of which can be monitored and controlled in accordance with aspects of the present invention.

Referring now to FIG. 6, there is illustrated a sectional view of a bulk MOSFET device 600 the silicidation process of which can be monitored and controlled in accordance with aspects of the present invention. Feature sizes of 0.12 $\mu$m are already possible. Scaling down to smaller and smaller feature sizes continues to introduce complexities that require automated control features. In support thereof, automated process control of the silicidation processes associated therewith, as provided by the subject invention, becomes increasingly important.

The bulk device 600 includes a silicon substrate 602 into which a source region 604 and a drain region 606 are diffused. A source implant junction 608 is associated with the depth of the diffused source region 604. Similarly, a drain implant junction 610 associated with the depth of the diffused drain region 606.

A gate oxide layer 612 is formed over the source and drain regions (604 and 606) and a portion of the substrate 602 to provide insulation from a polycrystalline silicon gate structure 614.

The silicidation process includes formation of a silicide 616 over portions of the source and drain regions (604 and 606), as well as over the poly gate structure 614. The silicide 616 at the source region is formed to a depth defined by a source silicide junction 618, and the silicide 616 at the drain region is formed to a depth defined by a drain silicide junction 620. Since silicide formation at both the source and drain occurs at substantially the same rate, the depth of the source silicide junction 618 and depth of the drain silicide junction 620 are the same or nearly the same.

The silicidation processes for both the source and drain regions (604 and 606) are monitored and controlled in accordance with the feedback system of the present invention. In one implementation, the disclosed system can monitor formation in both regions substantially simultaneously and then use the rate of silicide formation diffusion and silicide junction depth in a region (source or drain) that is the fastest (or the slowest, or both) to dictate when to stop the process. In another implementation, the system can measure the source silicide junction depth and the drain silicide junction depth as formation progresses, and then average the monitored values to arrive at the state of the silicidation process. In yet another implementation, the system may be configured to measure rate and/or depth information in only one region, either the source region 604 or the drain region 606. In still another implementation, the system can monitor the state of silicidation according to an interleaved process where in one monitor cycle, silicidation of the source is measured, and in the next cycle silicidation of the drain is measured.

In a more robust implementation, the system can invoke various implementations according to the state of the silicidation process. For example, when formation begins, the system can automatically invoke a more "relaxed" monitor and control scheme where silicidation is monitored and controlled in only the source region 604 or the drain region 606. As the expected completion time approaches, and at a predetermined time, the system can then automatically switch to monitoring silicidation according to a more "stringent" scheme where both the source and drain regions are monitored, using, for example, the averaging method.

A spacer material 622 (e.g., a low temperature dielectric spacer such as a nitride or any suitable insulator, where the insulating material is deposited by chemical vapor deposition) is then formed on the gate structure 614.

In one embodiment, the source silicide junction depth is approximately one-half of the source implant junction depth 608 (which is about the same for the drain region 606). Thus, the system of the present invention monitors and controls silicide formation such that the lower edge of the silicide formation diffuses to the desired depth, for example, approximately one half the depth of the source implant junction 608, and then stops.

A typical implant junction depth (for both the source and drain) can range from about 50 nm to about 150 nm. In one embodiment, the depth of the silicide formed in accordance with the present invention is from about 10 nm to about 140 nm. In another embodiment, the depth of the suicide formed in accordance with the present invention is from about 20 nm to about 130 nm. In yet another embodiment, the depth of the suicide formed in accordance with the present invention is from about 30 nm to about 120 nm.

A tolerance factor is the difference between the desired suicide depth and the actual silicide depth. The present invention provides desirable tolerance factors. In one embodiment, the tolerance factor is about 15 nm or less. In another embodiment, the tolerance factor is about 10 nm or less. In yet another embodiment, the tolerance factor is about 5 nm or less.

In these particular embodiments, the tolerance factor is about ten percent of the implant junction depth. For example, at a desired silicide junction depth of about 25 nm, the monitor and control system controls the annealing process to diffuse the silicide to within about 5 nm of the desired depth. That is, the silicide junction depth can range from about 20 nm to about 30 nm. For an implant junction depth of about 150 nm, the desired silicide junction depth is about 75 nm with a tolerance factor of 15 nm, resulting in a desired silicide junction depth ranging from about 60 nm to about 90 nm.

Figure 7:
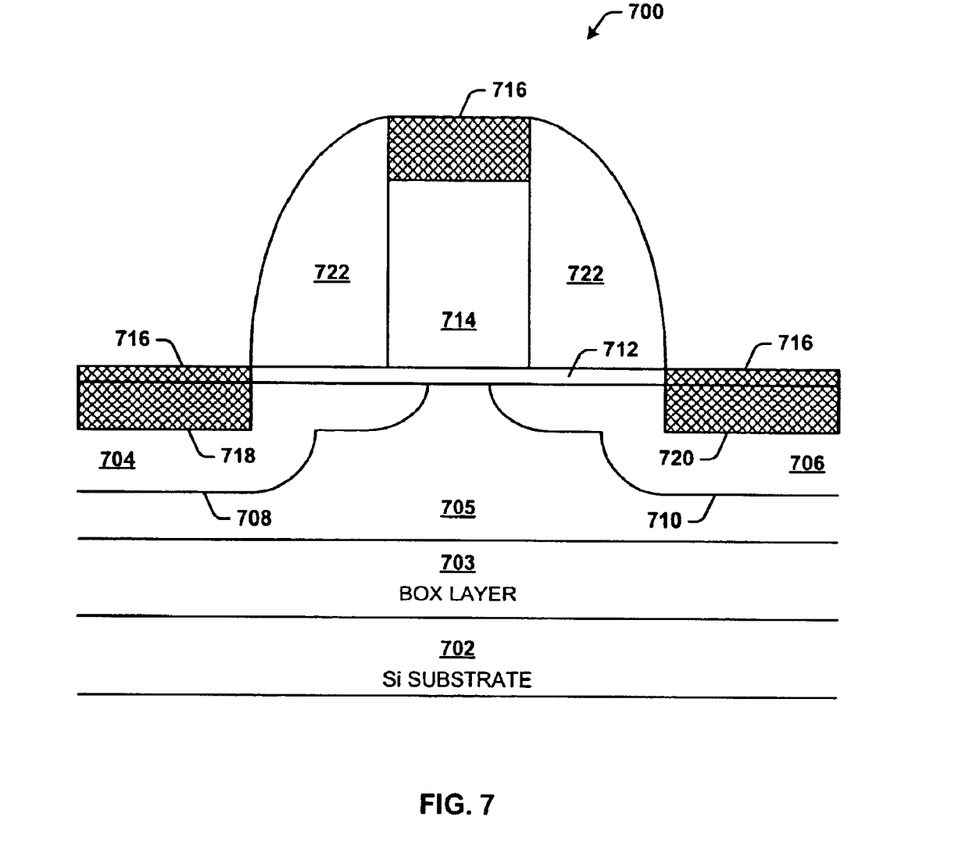
FIG. 7 illustrates a sectional view of an SOI MOSFET device the silicidation process of which can be monitored and controlled in accordance with aspects of the present invention.

Referring now to FIG. 7, there is illustrated a sectional view of an SOI (Silicon On Insulator) MOSFET device 700 the silicidation process of which can be monitored and controlled in accordance with aspects of the present invention. The SOI MOSFET device 700 presents several advantages over the bulk MOSFET device 600, such as larger integration density and smaller short channel effects. However, even with the higher densities and shorter channels, the system of the present invention can monitor and control the silicidation process.

The device 700 includes a silicon substrate 702 over which buried oxide (BOX layer 703 is formed. A silicon film layer 705 is formed over the BOX layer 703 and into which a source region 704 and a drain region 706 are diffused. A source implant junction 708 is associated With the depth of the diffused source region 704. Similarly, a drain implant junction 710 associated with the depth of the diffused drain region 706.

A gate oxide layer 712 is formed over the source and drain regions (704 and 706) and a portion of the film layer 705 to provide insulation from a polycrystalline silicon gate structure 714.

The silicidation process includes formation of a silicide 716 over portions of the source and drain regions (704 and 706), as well as over the poly gate structure 714. The silicide 716 at the source region 704 is formed to a depth defined by a source silicide junction 718, and the silicide 716 at the drain region 706 is formed to a depth defined by a drain silicide junction 720. Since silicide formation at both the source and drain occurs at substantially the same rate, the depth of the source silicide junction 718 and depth of the drain silicide junction 720 are the same or substantially the same.

A spacer material 722 (e.g., a low temperature dielectric spacer such as a nitride or any suitable insulator, where the insulating material is deposited by chemical vapor deposition) is then formed on the gate structure 714.

The junction depths, tolerance factors and, monitor and control aspects associated with FIG. 6, also apply here to the SOI MOSFET device, and are not repeated here, for brevity. It is to be appreciated that the depth of the silicide junction can be controlled with the system of the present invention to a depth and tolerance according to the particular process implementation. Of course, it is important to control the silicidation process to ensure that the annealing does not totally diffuse to the junction depth of the source/drain regions as this would severely impair the usefulness of the device, or even render the device useless.

It is further to be appreciated that a salicide may also be utilized in accordance with the system of the present invention.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the "comprising" as "comprising" is interpreted when employed as a transitional word a claim.

What is claimed is:

1. A system that facilitates control of a semiconductor process, comprising:
   a control subsystem that controls at least a silicidation process of a semiconductor substrate; and
   an analysis subsystem that analyzes a portion of the substrate at least in part during the silicidation process and sends a signal to the control subsystem, the analysis subsystem utilizing an interferometer.

2. The system of claim 1, the analysis subsystem is a Fourier Transform Infrared (FTIR) analysis subsystem.

3. The system of claim 1, the analysis subsystem is an ultraviolet FTIR analysis subsystem.

4. The system of claim 1, the analysis subsystem sends the signal to the control subsystem to stop the silicidation process.

5. The system of claim 1, the silicidation process includes a rapid thermal annealing (RTA) process.

6. The system of claim 1, the control system controls silicide formation of the silicidation process with a tolerance factor of about 5 nm or less.

7. The system of claim 1, the silicidation process utilizes a silicide selected from the group consisting of molybdenum, iron, platinum, niobium, hafnium, vanadium, zirconium, cobalt, titanium, and tantalum.

8. The system of claim 1, the silicidation process utilizes a metallic silicide.

9. The system of claim 1, the signal is transmitted from the analysis subsystem to the control subsystem via at least one of wired and wireless communication.

10. The system of claim 1, the signal transmitted to the control subsystem initiates an orderly shutdown of the silicidation process.

11. The system of claim 1, the control subsystem further comprises a monitor and control subsystem for monitor and control of the analysis subsystem, and a process control subsystem for monitor and control of the silicidation process.

12. The system of claim 11, the monitor and control subsystem receives the signal and sends a corresponding signal to the process control subsystem to initiate shutdown thereof.

13. The system of claim 11, the monitor and control subsystem includes a microscope for viewing a point of inspection of the substrate during the silicidation process.

14. The system of claim 11, the monitor and control subsystem includes a presentation component that presents to a user a view of a point of inspection of the substrate during the silicidation process.

15. The system of claim 11, the monitor and control subsystem includes a database of spectra data used to determine a state of the silicidation process.

16. The system of claim 1, the analysis subsystem performs analysis of silicide formation during the silicidation process.

17. The system of claim 1, the control subsystem automatically controls a sampling rate of the analysis subsystem during the silicidation process.

18. The system of claim 1, the control subsystem automatically varies a sampling rate of the analysis subsystem in accordance with the time remaining to complete the silicidation process.

19. The system of claim 1, the control subsystem controls the silicidation process to diffuse the silicide to about one-half of a source junction depth.

20. The system of claim 1, the control system controls suicide formation of the silicidation process to a depth from about 10 nm to about 140 nm.

21. The system of claim 1, the control system controls silicide formation of the silicidation process with a tolerance factor of about 15 nm or less.

22. The system of claim 1, the control system controls suicide formation of the silicidation process to a depth from about 20 nm to about 130 nm with a tolerance factor of about 10 nm or less.

23. A system that facilitates control of a semiconductor process, comprising:
   means for controlling a silicidation process on a semiconductor substrate;
   means for analyzing a portion of the substrate during the silicidation process, the analyzing means comprises means for analyzing the silicidation process with an interferometer;
   means for determining a state of the silicidation process based upon the portion analyzed; and
   means for sending a signal to control the silicidation process based upon the state.

24. The system of claim 23, the analyzing means is an FTIR spectroscopy subsystem.

25. The system of claim 23, the analyzing means comprises means for detecting a wavelength of light emitted from a light source through the substrate.

26. A method of controlling a semiconductor process, comprising:
controlling a silicidation process on a semiconductor substrate;
determining a state of the process based upon the substrate analysis; and
sending a signal to control the process based upon the state, the signal is sent in response to the process state determined to be within a ten percent tolerance factor of a desired silicide junction depth.

27. The method of claim 26, the state of the process is determined using FTIR spectroscopy.

28. The method of claim 26, the process includes an RTA process.

29. The method of claim 26, the signal stops the process.

30. The method of claim 26, the control system controls silicide formation of the silicidation process to a depth from about 10 nm to about 140 nm.

31. The method of claim 26, further comprising analyzing the substrate at a plurality of locations to determine the state of the process.

32. The method of claim 26, further comprising comparing spectra data of the silicidation process with predetermined stored spectra data to determine the state of the process.

33. The method of claim 26, the process state is controlled such that the silicide formation does not exceed fifty percent of a source junction depth.

34. A method of controlling a semiconductor process, comprising:
controlling a silicidation process on a semiconductor substrate;
monitoring the silicidation process at; i) at both the source and drain regions substantially simultaneously or ii) at the source and drain regions interleavingly;
analyzing the substrate at a plurality of locations during the process;
comparing spectra data of the silicidation process with predetermined stored spectra data;
determining a state of the process based upon the compared spectra data; and
sending a signal to control the process based upon the state.

35. The method of claim 34, the state of the process is determined using FTIR spectroscopy.

36. The method of claim 34, the process includes an RTA process.

37. The method of claim 34, further comprising fabricating a grating structure at a polysilicon layer to facilitate analyzing the substrate.

38. The method of claim 34, the state of the process based upon at least a depth of a silicide used in the silicidation process.

39. The method of claim 38, the depth of the silicide not to exceed one-half of the deep implant junction depth.

40. The method of claim 34, the silicidation process is applied to fabrication of at least one of a bulk MOSFET device and an SOI MOSFET device.

41. The method of claim 34, further comprising monitoring the silicidation process at both the source and drain regions substantially simultaneously.

42. The method of claim 34, further comprising monitoring the silicidation process at the source and drain regions interleavingly.

43. The method of claim 34, the silicidation process is controlled to form silicide to a depth from about 30 nm to about 120 nm with a tolerance factor of about 5 nm or less.

44. A system that facilitates control of a semiconductor process, comprising:
a control subsystem that controls at least a silicidation process of a semiconductor substrate, the control system controls silicide formation of the silicidation process to a depth from about 10 nm to about 140 nm; and
an analysis subsystem that analyzes a portion of the substrate at least in part during the silicidation process and sends a signal to the control subsystem.

* * * * *